United States Patent [19]

Marin et al.

[11] Patent Number: 5,456,694
[45] Date of Patent: Oct. 10, 1995

[54] DEVICE FOR DELIVERING AND DEPLOYING INTRALUMINAL DEVICES

[75] Inventors: Michael L. Marin; Ralph Marin, New York, N.Y.

[73] Assignee: Stentco, Inc., Cross River, N.Y.

[21] Appl. No.: 243,190

[22] Filed: May 13, 1994

[51] Int. Cl.⁶ ............................................... A61M 29/00
[52] U.S. Cl. ............................ 606/198; 606/194; 604/96; 623/1; 623/12
[58] Field of Search ................................. 606/108, 191, 606/192, 194, 195, 198, 200; 623/1, 12; 128/898, 899; 604/94–101

[56] References Cited

U.S. PATENT DOCUMENTS

| | | |
|---|---|---|
| 832,201 | 10/1906 | Kistler . |
| 1,737,488 | 11/1929 | Zohlen . |
| 2,684,069 | 7/1954 | Donaldson et al. . |
| 3,495,586 | 2/1970 | Regenbogen . |
| 3,517,128 | 6/1970 | Hines . |
| 3,557,794 | 1/1971 | Van Patten . |
| 3,704,712 | 11/1972 | Giesy et al. . |
| 3,968,800 | 7/1976 | Vilasi . |
| 3,996,938 | 12/1976 | Clark, III . |
| 4,168,709 | 9/1979 | Bentov . |
| 4,299,226 | 11/1981 | Banka ........................ 606/194 |
| 4,320,762 | 3/1982 | Bentov . |
| 4,577,631 | 3/1986 | Kreamer . |
| 4,585,000 | 4/1986 | Hershenson . |
| 4,648,402 | 3/1987 | Santos . |
| 4,655,771 | 4/1987 | Wallsten . |
| 4,921,484 | 5/1990 | Hillstead . |
| 4,969,890 | 11/1990 | Sugita et al. ................ 606/152 |
| 4,990,151 | 2/1991 | Wallsten . |
| 4,990,155 | 2/1991 | Wilkoff . |
| 5,064,434 | 11/1991 | Haber . |
| 5,074,871 | 12/1991 | Groshong . |
| 5,108,416 | 4/1992 | Ryan et al. .................. 623/1 |
| 5,221,258 | 6/1993 | Shturman . |
| 5,226,889 | 7/1993 | Sheiban ....................... 606/194 |
| 5,266,073 | 11/1993 | Wau .............................. 606/195 |
| 5,275,622 | 1/1994 | Lazarus et al. .............. 604/96 |
| 5,324,262 | 6/1994 | Fischell et al. . |

FOREIGN PATENT DOCUMENTS 0505686  9/1952  European Pat. Off. ............... 623/1

Primary Examiner—Stephen C. Pellegrino
Assistant Examiner—William Lewis
Attorney, Agent, or Firm—Darby & Darby

[57] ABSTRACT

A device for delivering and deploying a graft stent complex comprises a flexible guide sheath, the outer diameter of the guide sheath being constant throughout its length and the inner diameter of the guide sheath increasing from the proximal end to the distal end. A hemostatic valve having at least two ports is attached to the proximal end of the guide sheath, one port adapted to permit passage of a catheter into the guide sheath and the other port adapted to permit passage of a fluid into the guide sheath. A lead balloon catheter extends through the first port into the guide sheath, and includes an inflatable lead balloon at its distal end. A portion of the lead balloon extends from the distal end of the guide sheath to provide a tapered leading surface and also to seal the distal end of the guide sheath. Deployment means are provided within the guide sheath, with the stent being mounted on the deployment means. The deployment means includes an elongated shaft having a guide wire lumen disposed in colinear relationship with the guide wire lumen of the lead balloon catheter. Fluid may be applied under pressure to the second port of the hemostatic valve to vary the flexibility of the guide sheath.

21 Claims, 6 Drawing Sheets

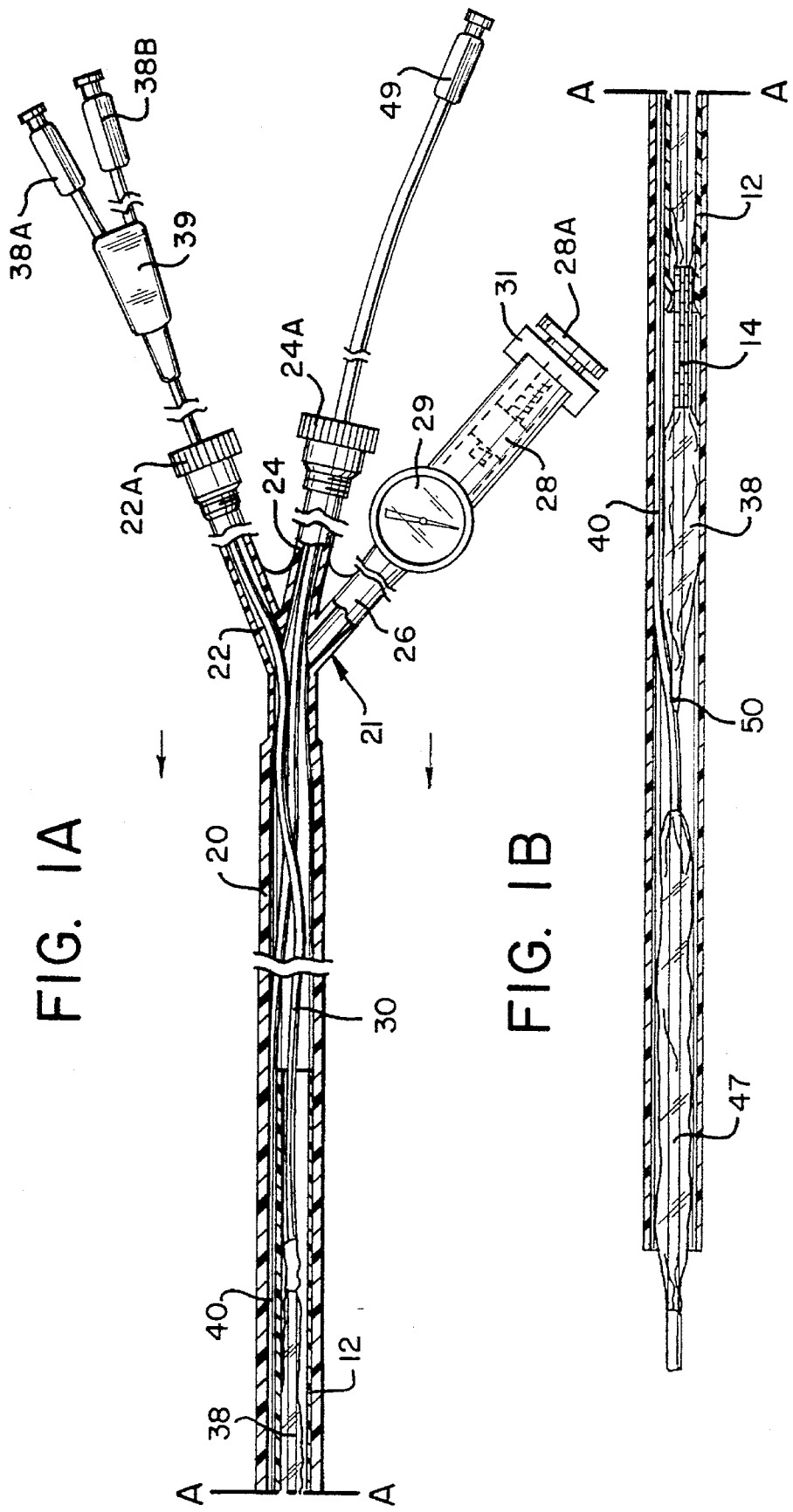

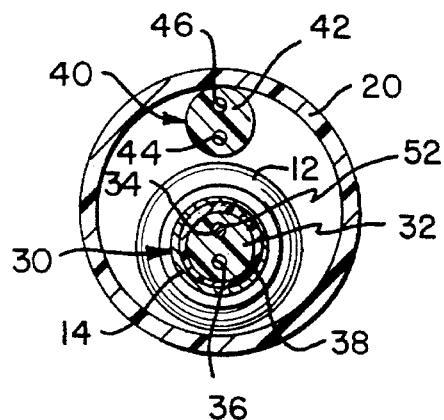
FIG. 3
FIG. 4
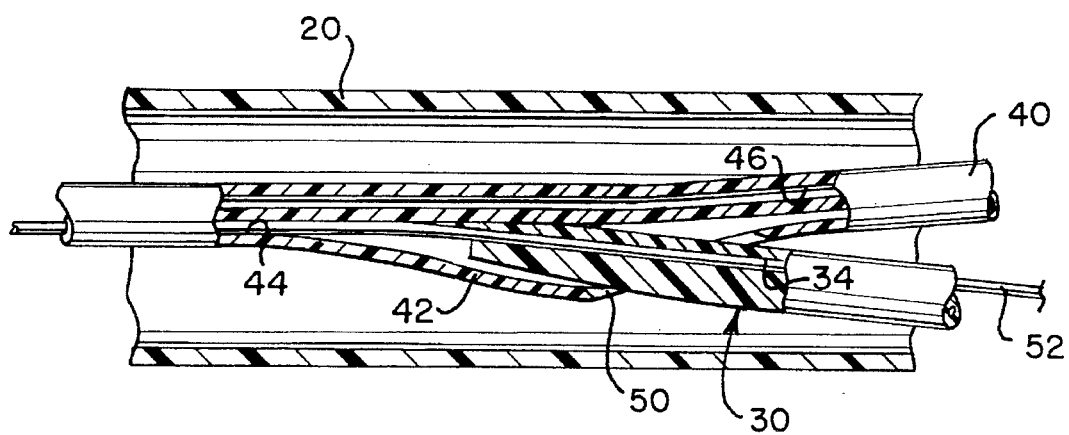

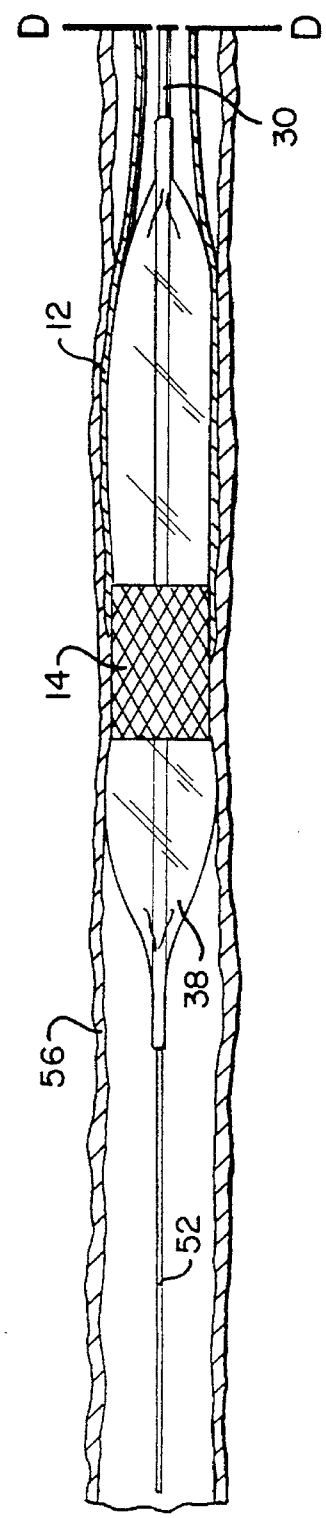
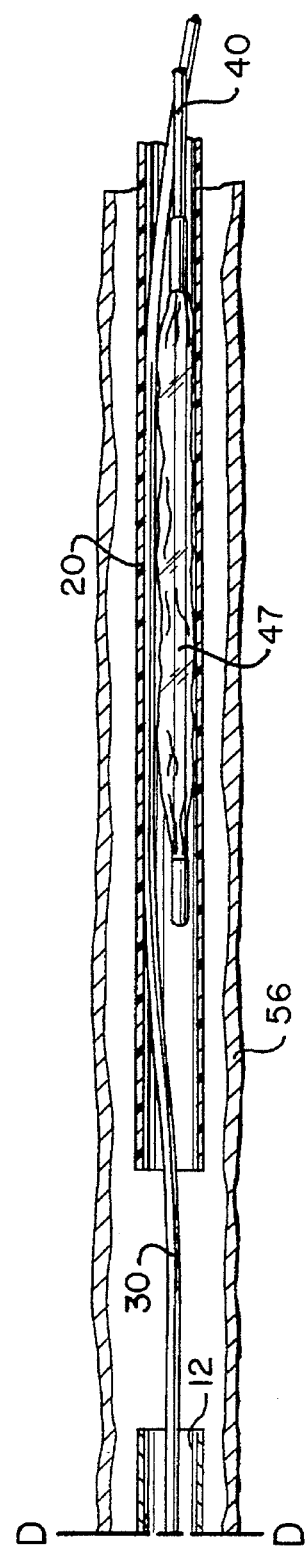

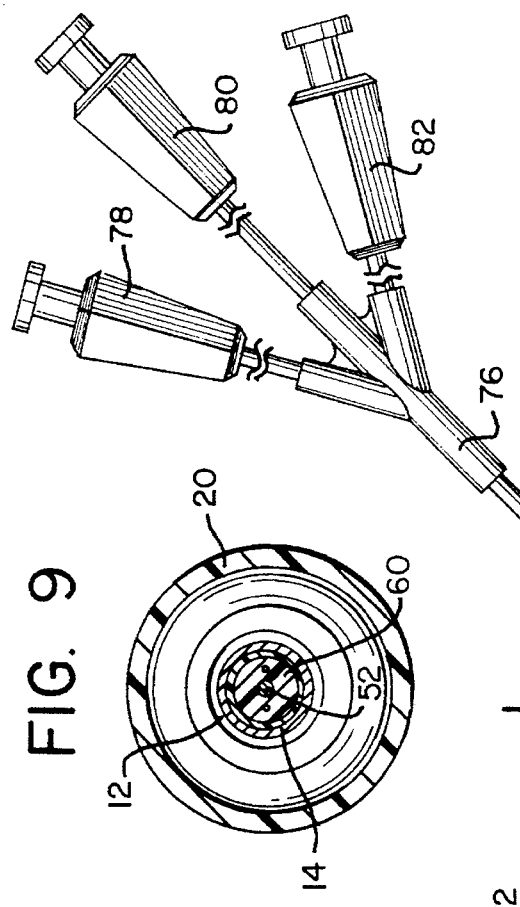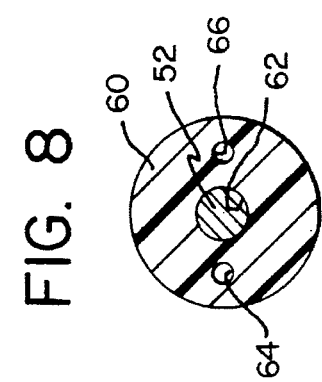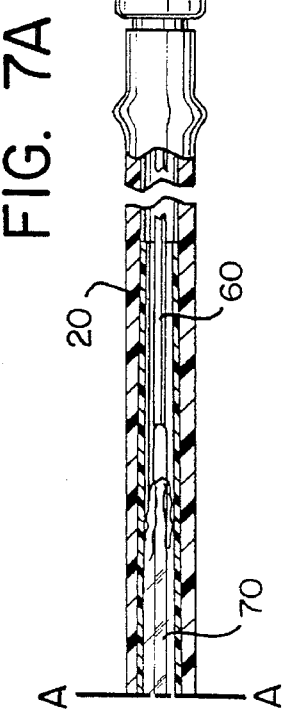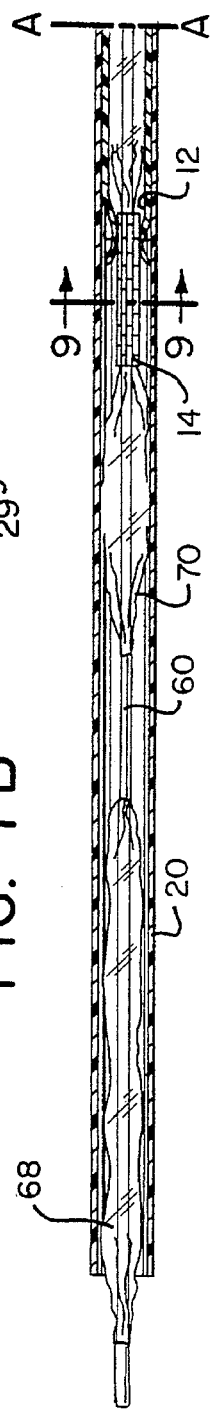
FIG. 9
FIG. 8
FIG. 7A
FIG. 7B

DEVICE FOR DELIVERING AND DEPLOYING INTRALUMINAL DEVICES

This invention relates to a device for delivering and deploying an intraluminal device. The invention has particular utility as a device for delivering and deploying stents and endovascular grafts within a blood vessel.

An endovascular graft is placed within a blood vessel and serves as a conduit for blood flow to exclude a vascular occlusion, aneurysm or other vessel abnormity. It may be made of a variety of materials, but most commonly is made of dacron, expanded polytetrafluoroethylene (ePTFE) or human vein. It is necessary to anchor the graft within the lumen of the blood vessel and this can be accomplished by means of an intravascular stent which is also commonly used to hold open diseased or occluded arteries. There are a number of known stents. Some are of the self-expanding type and some are made of a material (for example metal) which can be expanded after the stent is in place to frictionally engage the blood vessel. Palmaz U.S. Pat. No. 4,776,337 illustrates in FIGS. 2A and 2B a stent of the latter type which is currently in use. As used herein, the term "graft stent complex" is intended to include the combination of a graft and one or more stents.

The delivery and deployment systents for a graft stent complex typically include a guide sheath (catheter) which is properly positioned within the vasculature to guide the passage of a deployment mechanism (commonly a balloon catheter supporting the graft stent complex) to the proper site. The guide sheath has a relatively large diameter resulting in difficulty passing the sheath through arteries which usually are not straight and may have many curves or twists in them. Also, arteries may contain areas of disease (atherosclerotic plaque) which may obstruct the passage of the guide sheath through the vascular tree. Irregularly shaped plaque which could accidently engage an endoluminal catheter may create potential sites for arterial injury. Further, the vasculature may contain segments which are weaker than others, putting them at risk for perforation should they engage the guide sheath as it is being moved along the arterial wall.

The conventional technique for positioning a guide sheath within a blood vessel requires the use of a stylet (or mandrel or stiffening catheter as it is sometimes called), which includes a tapered distal end extending from the distal end of the guide sheath to enhance pushability of the guide sheath while providing a tapered distal face to ease passage of the guide sheath through the artery. The stylet, however, does not completely cover the relatively sharp edges of the guide sheath. Patients, therefore, are subject to arterial injury, and dislodgement of intraluminal thrombus and accumulated plaque on the arterial wall. This can lead to severe injury. Moreover, there is a trade-off between stiffness and flexibility. If the sheath is too stiff, movement through the artery is difficult. If it is too flexible, the sheath is difficult to push. Since the flexibility of the stylet is not adjustable, passage of the catheter through sharp turns in the vasculature can be very difficult, if not impossible. For example, the iliac artery is commonly kinked in patients with aortic aneurysm disease because of the frequent elongation of the vasculature during formation of the aneurysm. Manipulation of a wide guide sheath through such an artery using conventional techniques can be exceedingly difficult.

Also, conventional guide sheaths need to be large enough to permit ease of movement of an endovascular graft out of the sheath and into the vasculature. The sheath size has to be large enough to maintain a low coefficient of friction between the inner surface of the deployment catheter and the graft stent complex. Such large sheaths require large holes into the inserting blood vessel.

Finally, in the systents currently used for delivering a graft stent complex through a guide sheath, the balloon catheter containing the graft stent complex must be introduced through a hemostatic valve at the proximal end of the guide sheath and pushed through the entire length of the guide sheath (for example about sixty cm) to the deployment position. This can prove to be time consuming and difficult. In addition, the stent can be dislodged from the balloon while being pushed through the long guide sheath. This can result in the sharp metal stent perforating the deployment balloon. In either case, it is necessary to withdraw the balloon catheter and repeat the procedure.

OBJECTS OF THE INVENTION

The main object of the invention is to provide an improved device for delivering and deploying an endovascular stent and/or graft stent complex.

Another object is to provide a device for delivering and deploying a stent and/or graft stent complex which avoids or at least reduces the foregoing drawbacks of prior art stent delivery and deployment systents.

A still further object is to provide a device for delivering and deploying a stent and/or graft/stent complex in which the profile (diameter) of the device is reduced for a given size prosthesis.

SUMMARY OF THE INVENTION

According to the invention, a device for delivering and deploying a stent comprises a guide sheath and a lead balloon catheter within the guide sheath. At least the distal section of the guide sheath is made of a thin, flexible material so that the stiffness and flexibility of that action can be varied by applying fluid pressure to the sheath. The lead balloon catheter contains a lead balloon at its distal end which extends partially from the distal end of the guide sheath. When the lead balloon is inflated, it provides a tapered surface at the distal end of the guide sheath which may merge smoothly with the outer surface of the guide sheath, thereby reducing the likelihood of accidental arterial injury or dislodgement of thrombus or plaque. Fluid under pressure can be applied to the sheath to stiffen the sheath in a controlled fashion so that it can be pushed through the patient's vasculature. The invention provides for varying the pressure applied to the sheath so that the trade-off between pushability and flexibility can be optimized for the specific conditions of the vasculature on a moment by moment basis.

In the one embodiment, a balloon catheter is used to deploy the stent, although mechanical deployment means or self expanding deployment means may be used as well. The stent is mounted on the deployment means which is movable with the stent to a position distal of the guide sheath when the stent is to be deployed. A single catheter shaft supporting both the deployment and lead balloons may be used, but it is also contemplated that a deployment catheter separate from the lead balloon catheter may be used. In the latter case, an opening is provided in the lead balloon catheter shaft and the distal end of the deployment catheter is inserted into the opening in such a way that a guide wire inserted into the distal end of the lead balloon catheter shaft will pass automatically into the guide wire lumen of the deployment balloon catheter.

The invention provides a number of significant advantages as compared to prior art devices for delivering and deploying a stent. First of all, a stylet (or mandrel) is not required to position the sheath. Secondly, the ability to control the trade-off between stiffness and flexibility by pressurizing the guide sheath enables the operator to optimize the compromise between these two parameters depending on the patient's vasculature; moreover, since the pressurization of the sheath can be varied at will, the operator can change the trade-off as the sheath traverses the artery. That is, in tortuous sections, flexibility (steerability) can be favored at the expense of pushability. In straighter, more distal portions of the vasculature, the sheath can be stiffened to enhance pushability. This is particularly beneficial when encountering sharp turns as can occur in the iliac artery of patients suffering aortic aneurysm disease.

Because the sheath is pressurized, the wall of the sheath, particularly in the distal region, can be extremely thin. This increases the potential internal diameter of the sheath relative to the outer diameter and thereby increases the space available to house the graft or graft stent complex; this means that for a given outer diameter, the invention is capable of delivering and deploying a larger stent (or graft stent complex) than is possible in the prior art.

A valuable benefit of the invention is the fact that the sheath can be muzzle loaded with a graft stent complex prior to use. This provides two important advantages over conventional prior art techniques, wherein the graft stent complex is introduced through the proximal end of the sheath after the sheath is in position. In the first place, it avoids the need to traverse the entire length of the guide sheath to position the graft stent complex within the sheath. Secondly, since it is not necessary to introduce the complex through the hemostatic valve at the proximal end of the guide sheath, a smaller hemostatic valve can be used resulting in less blood loss during catheter manipulations.

A further feature of the invention resides in the fact that the use of a lead balloon results in a completely smooth transition between the distal face of the guide sheath and the tapered surface formed by the balloon. This smooth transition avoids the sharp edges which may exist when a stylet systent is used, and which may injure the artery and cause dislodgement of intraluminal thrombus and accumulated plaque.

IN THE DRAWINGS

FIGS. 1A and 1B comprise a plan view, partially in section, of a first embodiment of the invention assembled and ready for use prior to lead balloon inflation and sheath pressurization.

FIG. 3 is a cross sectional view along the line 3—3 of FIG. 2B;

FIG. 4 is an enlarged side sectional view showing the manner in which the distal end of the deployment catheter is joined to the lead balloon catheter;

FIGS. 6A and 6B are slightly enlarged views showing the balloons after the deployment balloon has been inflated to expand the distal stent with the deflated lead balloon previously retracted into the sheath.

Figure 2A:
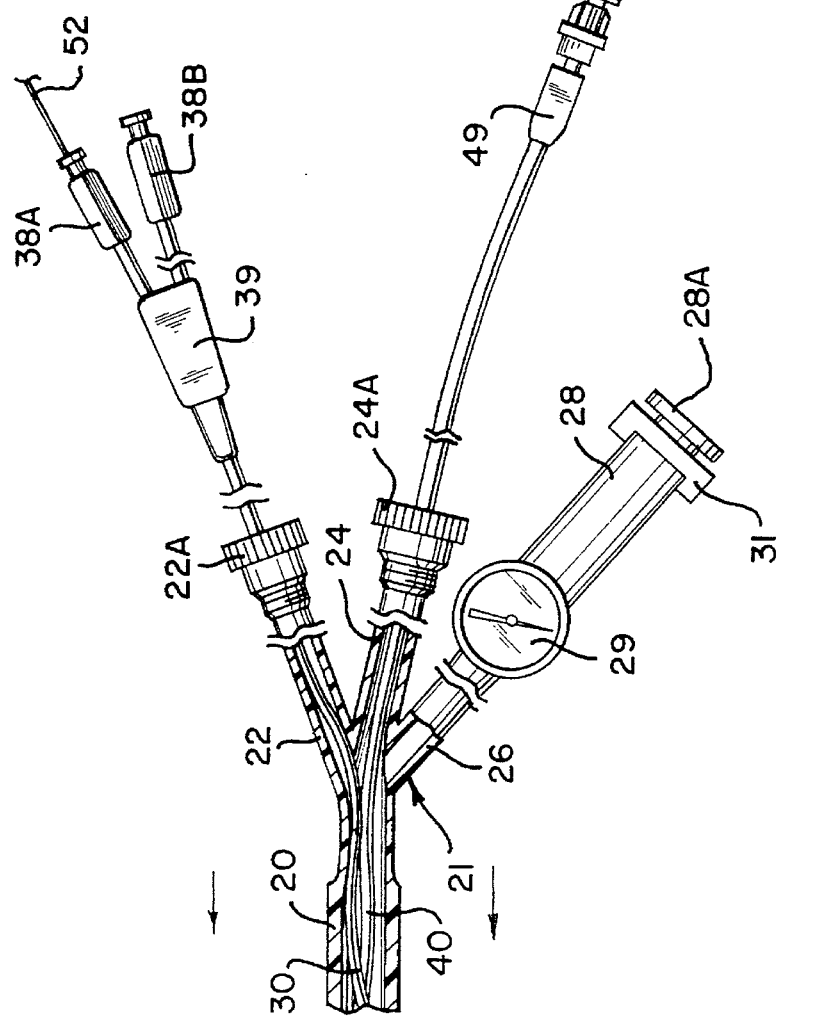
FIGS. 2A and 2B are slightly enlarged views of the proximal and distal ends, respectively, of the device shown in FIGS. 1A and 1B with a guide wire in place and the lead balloon at the distal end of the guide sheath inflated.

FIGS. 7A and 7B comprise a plan view partially in section showing a second embodiment of the invention;

FIG. 8 is a sectional view along the line 8—8 of FIG. 7A; and

FIG. 9 is a sectional view along the line 9—9 of FIG. 7B.

DETAILED DESCRIPTION OF THE INVENTION

FIGS. 1–6 illustrate an embodiment of the invention in which separate deployment and lead balloon catheters are used to deploy a graft stent complex shown as comprising a graft 12 and stent 14. Stent 14, for example, may be a conventional Palmaz stent. The specific construction of the device to be deployed is not a feature of the invention.

The delivery and deployment device comprises a guide sheath 20 which is adapted to be positioned within the patient's vasculature to facilitate delivery of the graft stent complex to the location where it is to be deployed. The guide sheath 20 terminates at its proximal end in a three way hemostatic valve 21. Hemostatic valve 21 may be a modified Tuoy Borst hemostatic valve having deployment catheter port 22, an end catheter port 24 and a sheath pressurization port 26 for purposes described below. Hemostatic valve 21 prevents the loss of blood through sheath 20 when its distal end is not sealed. Thumb screws 22A and 24A close ports 22 and 24, also locking in position the catheter which passes through the port.

The sheath pressurization port 26 is connected through a syringe 28 which may be of the type which includes an integral infusion pressure manometer 29 to provide the operator with a continuous indication of the pressure applied by the syringe to the port 26. The syringe 28 may include a piston which is threadedly received within a bracket 31 fixed to the barrel. Pressure is applied by rotating a knob 28A at the end of the piston to advance the piston and apply very precise pressures to the sheath. Syringes of this type are conventional disposable items. The syringe may be integrally formed with the port 28, or the port and syringe may be provided with standard connecting means so that the parts can be selectively coupled together.

The guide sheath 20 contains a deployment catheter 30 and a lead balloon catheter 40. The deployment catheter 30 comprises an elongated flexible shaft 32 which includes a guide wire lumen 34 and an inflation lumen 36 (see FIG. 3). A deployment balloon 38 is mounted on the distal end of the deployment catheter 30 in such a way that it can be inflated and deflated through the inflation lumen 36.

The deployment balloon catheter 30 terminates at its distal end in luer locks 38A and 38B which are connected by means of a standard bifurcated connector 39 to the proximal end of the catheter shaft 32. The luer lock 38A is in fluid communication with the inflation lumen 36 and the luer lock 38B communicates with the guide wire lumen 34. Balloon catheters of this construction are conventional; therefore, the deployment catheter 30 is not described in further detail.

The lead balloon catheter 40 likewise is of conventional construction and includes an elongated flexible shaft 42 which includes a guide wire lumen 44 and an inflation lumen 46. A lead balloon 47 is mounted at the distal end of the catheter 40 and can be selectively inflated and deflated through the inflation lumen 46. A luer lock 49 is attached to the proximal end of the lead balloon catheter 40 so that the balloon 47 can be inflated by the introduction of fluid through the luer lock 49.

The lead balloon shaft 42 includes an opening 50 which, as most clearly shown in FIG. 4, is adapted to receive the distal end of the deployment catheter 30. Opening 50, which may be formed by skiving shaft 42, does not affect the inflation lumen 46 but enables the guide wire lumens 34 and 44 to be aligned in a substantially colinear relationship so that a standard guide wire 52 can be passed from the lead balloon catheter 40 to the guide wire lumen 34 of the deployment catheter 30 during use.

As shown schematically in the drawings, sheath 20 has a constant outer diameter, but the inner diameter of the proximal portion of the sheath (FIG. 1A) is less than the inner diameter of the distal portion (FIG. 1B), i.e. the distal section is more flexible (less stiff) and includes a wider lumen. The proximal portion of the sheath provides increased pushability and torquability of the catheter as it is inserted. Because the graft stent complex is muzzle loaded (as explained below), there is no need for a large internal diameter in the proximal segment of sheath 20 and a thicker wall is feasible.

In the distal portion of the sheath 20, the wall is thin and indeed, may even be flimsy, for example, comparable to cellophane film. Reduction of wall thickness in the distal portion of the sheath provides increased space in which the graft stent complex can be housed, which means that for a given outer diameter, a larger complex is possible with the invention. Pushability of the catheter is enhanced in part by the presence of the stent graft complex within the sheath but, primarily, the stiffness required is achieved by pressurizing the sheath by the introduction of fluid under pressure through port 26 of valve 21. By monitoring the pressure on a manometer 54 during insertion of the sheath, the surgeon can continuously vary the stiffness (and thus pushability and flexibility) of the sheath throughout the insertion procedure. This means that the surgeon has the capability of varying the stiffness of the catheter sheath during different phases of insertion depending on the degree of tortuosity of the vascular systent.

The sheath 20 may be made of PTFE (Teflon). The length and characteristics of the sheath will vary depending upon the particular application. Where an aortic aneurysm graft is to be deployed, the sheath 20 may be approximately 60 cm in length with the distalmost 15–20 cm comprising the flexible portion of the sheath. The sheath may be manufactured by standard extrusion techniques with the distal flexible portion thereafter cored from the extruded tube to form a thinner-walled flexible section.

The device may be assembled and sold in the condition shown in FIGS. 1A and 1B, or it may be assembled at the time of use. The method of assembly is as follows.

Deployment catheter 30 and lead balloon catheter 40 are passed through the deployment catheter port 22 and tip catheter port 24 of hemostatic valve 21 with the valve screws 22A and 22B open until the balloons 38 and 48 extend from the distal end of the sheath. If the device is to be used to deploy a graft stent complex 12, 14, the complex is then placed over the distal end of deployment catheter 30 with the balloon 38 beneath the stent 14. In conventional fashion, the stent 14 is crimped to balloon 38. The distal tip of deployment catheter 30 is then inserted into the opening 50 within the shaft 42 of lead balloon catheter 40 so that a continuous or colinear passageway is formed between the guide wire lumens 34 and 44.

Figure 2B:
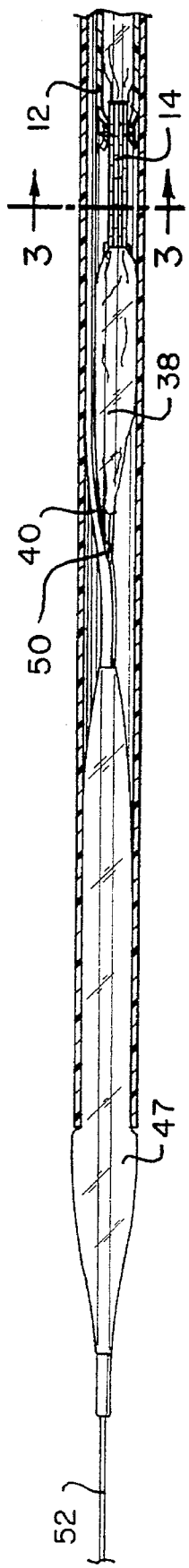

The graft stent complex and catheters 30 and 40 are then muzzle loaded into the sheath 20 (i.e., retracted proximally into the sheath) and positioned so that, for example, about half of the lead balloon 48 extends from the distal end of the sheath 20, as shown in FIG. 2B. The lead balloon 48 may be about four cm. in length which means that approximately two cm. of the balloon will extend distally from the sheath 20. The ability to muzzle load the catheters and graft-stent complex into the sheath is a valuable feature of the invention since it avoids the need to push the graft through the entire sheath which, in view of the length of the sheath, can be time consuming and may result in separation of the graft-stent complex (14,12) from the underlying balloon.

The device is used as follows. A one-way valve 51 (FIG. 2A) is attached to the lead balloon inflation port luer lock 49 and the lead balloon 48 inflated with saline solution from a standard ten cc. syringe 53 attached to luer lock 49. As shown in FIG. 2B, when the balloon 48 is inflated, it seals the distal end of the sheath 20 and provides a smooth taper which facilitates movement of the sheath through the patient's vasculature. Expansion of the balloon also results in a smooth transition between the sheath and balloon (see FIG. 2B) which means that the sheath is less likely to injury the artery or dislodge thrombus or plaque as it is pushed through the artery. The lead balloon also serves to aid in hemostasis, since blood cannot travel back through the sheath and out of the patient while the balloon is inflated.

The syringe 28 attached to the sheath pressurization port 26 is then used to inject saline into sheath 20 to a desired sheath pressure as measured by the infusion pressure manometer. After all air has been evacuated, i.e. the systent has been bled, the catheter infusion ports are closed. The device is now ready to be inserted into the patient.

The device is inserted as follows. First, the guide wire 52 is passed through the patient's vasculature with its location being confirmed fluoroscopically. In FIGS. 5A, 5B, 6A and 6B, a blood vessel is shown at 56 for purposes of explanation. The operator then inserts the proximal end of the guide wire into the distal end of the guide wire lumen 44 within lead balloon catheter 40. The operator next introduces sheath 20 into the patient over the guide wire. Because of the way in which the deployment catheter 30 is nested within the lead balloon catheter 40, the guide wire passes from the lead balloon guide wire lumen 44 into the colinear deployment guide wire lumen 34 as shown in FIG. 4. With the inflated lead balloon 48 providing a smooth taper for the pressurized sheath 22, the operator guides the sheath with the enclosed catheters to the location where the stent is to be deployed. As the sheath is being moved, the surgeon can vary its flexibility to accommodate the specific vasculature by adjusting the pressure within the sheath as indicated by manometer 54. The sheath position is determined fluoroscopically in a conventional fashion. For example, the sheath 20 may have regularly placed radiopaque markers so that the exact location of the sheath tip can be identified. When the proper location is reached, lead balloon 48 is deflated using the syringe.

Figure 5A:
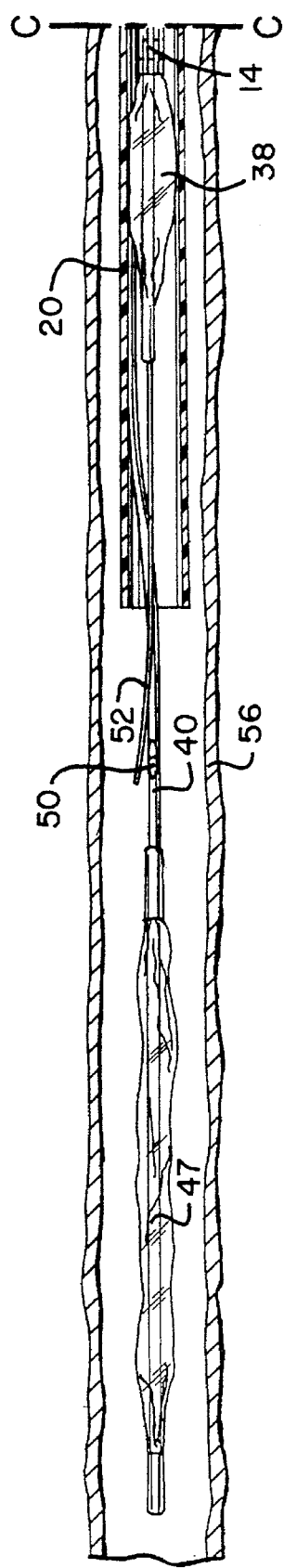
FIGS. 5A and 5B are slightly enlarged views showing the device with the deployment balloon positioned within the guide sheath and the lead balloon deflated and extended off and beyond the guide wire.
Figure 5B:
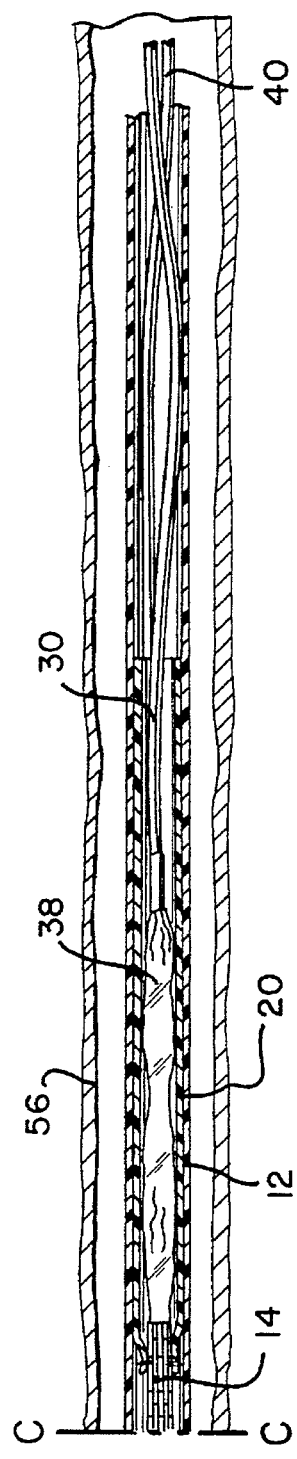

The thumbwheel 24A for the lead balloon catheter 40 is then released and the lead balloon catheter advanced distally (with the position of the deployment catheter 30 held in place) until the catheter 40 is disengaged from the guide wire 52 (FIGS. 5A and 5B). This occurs when the opening 50 moves distally beyond the distal end of the guide wire 52.

The surgeon then retracts the lead balloon catheter 40 back into the sheath 20 to a position proximal of the graft stent complex 12, 14 and tightens the thumb screw 24A to retain the lead. balloon catheter in this position.

Next, the thumb screw 22A which secures the deployment catheter 30 is loosened and the sheath 20 retracted to expose the stent 14. The syringe with saline is attached to the luer lock 38B and the deployment balloon 38 is expanded to deploy the stent (FIGS. 6A and. 6B). After the stent is fully deployed, the deployment balloon 38 is deflated. It may then be exchanged for a second deployment catheter containing a second stent to be properly positioned with respect to the graft 12 and deployed. Alternatively, graft 12 may be provided with both stents, in which case the deployment catheter 30 can be withdrawn until the deployment balloon 38 is beneath the second stent. The balloon can then be expanded to deploy the second stent. The sheath 20 and catheters 30 and 40 are then removed and a completion angiogram performed.

In the embodiment of FIGS. 7–9 only a single catheter is used. In this embodiment, the catheter comprises an elongated flexible shaft 60 having a central guide wire lumen 62 and peripheral inflation lumens 64 and 66. A lead balloon 68 is provided at the distal end of the catheter 60 for inflation through the lumen 64. A deployment balloon 70 is positioned on the shaft 60 proximally of the lead balloon 68 and adapted to be inflated or deflated by means of the lumen 66. The lead balloon 68 and deployment balloon 70 function the same way as the lead balloon 48 and deployment balloon 38 of the embodiment shown in FIGS. 1–6 but, of course, cannot be separated.

The proximal end of the guide sheath 20 terminates in a hemostatic valve 72 through which the catheter shaft 60 extends. The hemostatic valve 72 includes a port 74 which may be connected to the syringe 28 shown in FIG. 1A. The port 74, of course, provides access to the interior of the sheath 20. A standard hemostatic valve may be used as valve 72.

The catheter shaft 60 terminates in a conventional trifurcated fitting 76 having three proximal ports which terminate in luer lock 78, 80, and 82. The luer locks 78 and 82 provide access to the inflation lumens 64 and 66, respectively, while the luer lock 80 provides access to the guide wire lumen 62. In this case the guide wire 52 is inserted in conventional fashion through the guide wire lumen 62 of the catheter shaft 60. A one-way valve would be connected to luer lock 78 to maintain the inflation of the lead balloon during use.

The components illustrated may be conventional. For example, hemostatic valve 21 may be an ANGEDAPT Y-connector manufactured by Angeion Medical Products, Model No. AYC-020. Hemostatic valve 72 may be of the type sold by Universal Medical Instrument Corp. under the trademark CATH-SEAL (Model No. 1200- 90-3003). The pressure syringe 28 may be a LeVeen disposable inflation syringe with pressure gauge manufactured by the MedTech Division of Boston Scientific (Model No. 15-101).

In the illustrated embodiments, the guide sheath comprises a relatively stiff flexible portion and a relatively flexible distal portion. It is conceivable that it may prove beneficial to have a continuously variable change in stiffness/flexibility, in which case the inner wall may taper gradually with the diameter increasing from the proximal end to the distal end. It is also possible that stiffness/flexibility may vary in a number of discrete steps, rather than in a single step as illustrated.

It is also contemplated that the entire sheath can be made of a highly flexible plastic (e.g., PTFE), which can be folded so as to reduce its cross section prior to insertion. The advantage of this construction is that a small introducer (and thus a smaller hole in the patient's artery) could be used to introduce the sheath into the patient's artery. Once in position, the sheath would be pressurized as described in the foregoing to increase its diameter as required for delivery and deployment of the stent.

In addition to varying the pressure of the sheath as it passes through the patient's vasculature, it is also possible to vary the pressure applied to the lead balloon so that the operator can vary the flexibility of the leading surface of the sheath as it traverses the vasculature, should this be desirable.

Many modifications of the illustrated embodiments are possible within the scope of the invention. For example, the stent deployment means may comprise a mechanical device rather than a balloon. One suitable device for mechanically deploying a stent is shown in copending U.S. patent application Ser. No. 08/196,278, filed Feb. 10, 1994, in the names of Michael and Ralph Marin, and entitled APPARATUS AND METHOD FOR DEPLOYMENT OF RADIALLY EXPANDABLE STENTS BY A MECHANICAL LINKAGE.

Furthermore, although the invention has been described for use in the delivery and deployment of stents and graft stent complexes, the broad principles of the invention can be used in the delivery and/or deployment of other intraluminal devices such as but not limited to VenaCava filters, atherectomy devices and the like.

What is claimed is:

1. A device for delivering and deploying a graft stent complex, comprising:
   a flexible guide sheath having proximal and distal ends, the outer diameter of said guide sheath being substantially constant throughout its length and the inner diameter of the proximal end of said guide sheath being less than the inner diameter of the distal end;
   a hemostatic valve having at least two ports attached to the proximal end of said guide sheath, one port adapted to permit passage of a catheter into said guide sheath and the other port adapted to permit passage of a fluid into said guide sheath;
   a lead balloon catheter extending through said one port into said guide sheath, said lead balloon catheter including a guide wire lumen, an inflation lumen, and an inflatable lead balloon at its distal end, at least a portion of said lead balloon extending from the distal end of said guide sheath, said portion providing a tapered leading surface and sealing the distal end of said guide sheath when said lead balloon is inflated;
   a graff stent complex comprising a graft and at least one stent;
   deployment means within said guide sheath, the stent of said complex being mounted on said deployment means, said deployment means including an elongated shaft having a guide wire lumen passing therethrough and disposed in colinear relationship with the guide wire lumen of said lead balloon catheter; and
   means for applying fluid under pressure to said other port of said hemostatic valve to vary the flexibility of the guide sheath.

2. A device for delivering and deploying a graft stent complex according to claim 1, further including means for measuring the pressure of the fluid applied under pressure to said other port.

3. A device for delivering and deploying a stent according to claim 1, wherein the lead balloon catheter is separate from said deployment means.

4. A device for delivering and deploying a stent according to claim 3, wherein said lead balloon catheter includes a guide wire lumen and an opening, with the distal end of said deployment shaft extending through said opening into the guide wire lumen of said lead balloon catheter.

5. A device for delivering and deploying a stent according to claim 4, wherein said hemostatic valve includes a port through which said lead balloon catheter extends, a port through which fluid under pressure can be applied to said sheath, and a port through which said deployment means extends.

6. A device for delivering and deploying an intraluminal device, comprising:

a guide sheath having proximal and distal ends;

a lead balloon catheter within said sheath, said lead balloon catheter including an inflatable lead balloon at its distal end, the diameter of the lead balloon when inflated being greater than the inner diameter of said guide sheath and the distal portion of said lead balloon being tapered when the balloon is inflated, at least a portion of said lead balloon extending from the distal end of said guide sheath in such a way as to provide a tapered leading surface for said guide sheath and a fluid-tight seal at the distal end of said guide sheath when said lead balloon is inflated; and means for applying a fluid under pressure to said guide sheath to vary the flexibility of the guide sheath when said lead balloon has been inflated to seal the distal end of said guide sheath.

7. A device for delivering and deploying an intraluminal device according to claim 6, further including a stent and deployment means within said guide sheath for deploying said stent, said stent being mounted on said deployment means, said deployment means being movable with said stent to a position distal of said guide sheath for dipolymers of said stent within a blood vessel.

8. A device for delivering and deploying an intraluminal device according to claim 7, wherein said deployment means includes a shaft, expansion means beneath said stent, and a guide wire lumen passing through said shaft, and wherein said lead balloon catheter includes a guide wire lumen colinear with the guide wire lumen of said shaft, whereby a guide wire can pass through said lumens.

9. A device for delivering and deploying an intraluminal device according to claim 3, wherein the lead balloon catheter is separate from said deployment means.

10. A device for delivering and deploying an intraluminal device according to claim 4, wherein said lead balloon catheter includes a guide wire lumen and an opening, with the distal end of said deployment shaft extending through said opening into the guide wire lumen of said lead balloon catheter.

11. A device for delivering and deploying an intraluminal device according to claim 7, including a hemostatic valve connected to the proximal end of said guide sheath, said hemostatic valve including a port through which said lead balloon catheter extends and a port through which fluid under pressure can be applied to said sheath.

12. A device for delivering and deploying an intraluminal device according to claim 7, wherein the inner diameter of the proximal end of said guide sheath is greater than the inner diameter of the distal end.

13. A method of assembling a graft stent complex to a delivery and deployment device which comprises a guide sheath having distal and proximal ends, a lead balloon catheter for providing a tapered seal at the distal end of said guide sheath, and deployment means having an expandable member for deploying the stent, comprising the steps of:

introducing the lead balloon catheter and expandable member into the guide sheath through the proximal end of the guide sheath;

causing the lead balloon and expandable member to extend from the distal end of said guide sheath;

placing a stent over the expandable member, and retracting the lead balloon catheter and expandable member into the guide sheath through its distal end such that the entire stent is positioned within the guide sheath but at least a portion of the lead balloon extends from the distal end of said guide sheath.

14. A method of introducing a guide sheath into a blood vessel, at least a distal portion of said guide sheath being made of a soft flexible material, comprising the steps of sealing the distal end of said guide sheath with a lead balloon by inflating the lead balloon, and applying a fluid under pressure to the proximal end of said guide sheath to control the flexibility of the guide sheath.

15. A method according to claim 14, wherein the pressure applied to said guide sheath is varied as the guide sheath is pushed through the blood vessel to adjust the flexibility of the guide sheath.

16. A device for delivering and deploying an intraluminal device, comprising:

a guide sheath having proximal and distal ends;

a lead balloon catheter within said sheath, said lead balloon catheter including an inflatable lead balloon at its distal end, the diameter of the lead balloon when inflated being greater than the inner diameter of said guide sheath and the distal portion of said lead balloon being tapered when the balloon is inflated, at least a portion of said lead balloon extending from the distal end of said guide sheath in such a way as to provide a tapered leading surface for said guide sheath and a fluid-tight seal at the distal end of said guide sheath when said lead balloon is inflated;

a stent; and deployment means within said guide sheath for deploying said stent, said stent being mounted on said deployment means, said deployment means being movable with said stent to a position distal of said guide sheath for deployment of said stent within a blood vessel.

17. A device for delivering and deploying an intraluminal device according to claim 16, wherein said deployment means includes a shaft, expansion means beneath said stent, and a guide wire lumen passing through said shaft, and wherein said lead balloon catheter includes a guide wire lumen colinear with the guide wire lumen of said shaft, whereby a guide wire can pass through said lumens.

18. A device for delivering and deploying an intraluminal device according to claim 17, wherein the lead balloon catheter is separate from said deployment means.

19. A device for delivering and deploying an intraluminal device according to claim 18, wherein said lead balloon catheter includes a guide wire lumen and an opening, with the distal end of said deployment shaft extending through said opening into the guide wire lumen of said lead balloon catheter.

20. A device for delivering and deploying an intraluminal device according to claim 16, including a hemostatic valve connected to the proximal end of said guide sheath, said hemostatic valve including a port through which said lead balloon catheter extends and a port through which fluid under pressure can be applied to said sheath.

21. A device for delivering and deploying an intraluminal device according to claim 16, wherein the inner diameter of the proximal end of said guide sheath is greater than the inner diameter of the distal end.

* * * * *